US00PP22185P2

(12) United States Plant Patent
van Kleinwee

(10) Patent No.: US PP22,185 P2
(45) Date of Patent: Oct. 4, 2011

(54) *ARGYRANTHEMUM* PLANT NAMED 'ARGYMINYEL'

(50) Latin Name: *Argyranthemum frutescens*
Varietal Denomination: Argyminyel

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/807,519

(22) Filed: Sep. 8, 2010

(51) Int. Cl.
*A01H 5/00* (2006.01)

(52) U.S. Cl. ..... Plt./406

(58) Field of Classification Search ..... Plt./406
See application file for complete search history.

*Primary Examiner* — Kent L Bell
(74) *Attorney, Agent, or Firm* — S. Matthew Edwards

(57) ABSTRACT

A new *Argyranthemum* plant named 'Argyminyel' particularly distinguished by the yellow inflorescence color, medium green foliage, short peduncles, mounded and compact plant habit with good branching.

1 Drawing Sheet

Latin name of the genus and species of the plant claimed: *Argyranthemum frutescens.*

Varietal denomination: 'Argyminyel'.

BACKGROUND OF THE NEW PLANT

The present invention comprises a new *Argyranthemum*, botanically known as *Argyranthemum frutescens*, and hereinafter referred to by the variety name 'Argyminyel'.

'Argyminyel' is a product of a planned breeding program. The new cultivar has yellow inflorescence color, medium green foliage, short peduncles, mounded and compact plant habit with good branching.

'Argyminyel' originated from a hybridization made in July 2005 in a controlled breeding environment in Enkhuizen, Netherlands. 'Argyminyel' was derived from an open pollinated cross within the gene pool labeled 'C211-1', after several backcrosses were made. 'Argyminyel' has brighter yellow inflorescence color, better branching, smaller inflorescence diameter, is more floriferous and has an earlier flower season. The seed was collected in bulk and then sown in February 2006.

'Argyminyel' was selected as one flowering plant within the progeny of the stated cross in May 2006 in a controlled environment in Enkhuizen, Netherlands.

The first act of asexual reproduction of 'Argyminyel' was accomplished when vegetative cuttings were propagated from the initial selection in May 2006 in a controlled environment in Enkhuizen, Netherlands.

BRIEF SUMMARY OF INVENTION

Horticultural examination of plants grown from cuttings of the plant initiated in May 2006, and continuing thereafter, has demonstrated that the combination of characteristics as herein disclosed for 'Argyminyel' are firmly fixed and are retained through successive generations of asexual reproduction.

'Argyminyel' has not been observed under all possible environmental conditions. The phenotype may vary significantly with variations in environment such as temperature, light intensity and day length.

Plant Breeder's Right for this cultivar were applied for in Canada on Feb. 9, 2010 (10-6820) and in CPVO on Sep. 29, 2009 (2009/1912). 'Argyminyel' has not been made publicly available more than one year prior to the filing of this application.

The following traits have been repeatedly observed and are determined to be basic characteristics of the new variety. The combination of these characteristics distinguishes this *Argyranthemum* as a new and distinct variety.

BRIEF DESCRIPTION OF THE PHOTOGRAPHS

The accompanying photographic drawing shows typical flower and foliage characteristics of 'Argyminyel' with colors being as true as possible with an illustration of this type. The photographic drawing shows a flowering potted plant of the new variety and a close-up of the inflorescences.

DETAILED BOTANICAL DESCRIPTION

The aforementioned photographs were taken in April 2009 from plants growing in a greenhouse trial in Enkhuizen, Netherlands. These plants were growing in 4 inch pots and were approximately 12 weeks of age.

The plant descriptions and measurements were taken in mid-May 2010 in Hillscheid, Germany on 12 week old plants that had been planted into 12 cm pots. Rooted cuttings where potted and grown in the greenhouse at a minimum temperature of 12° C. day and night, from late April at a minimum temperature (heating temperature) of 8° C.

Color references are made to The Royal Horticultural Society Colour Chart (R.H.S.) 2001.

TABLE 1

DIFFERENCES BETWEEN THE NEW VARIETY 'ARGYMINYEL' AND A SIMILAR VARIETY

| | 'Argyminyel' | 'Argyrayesi' (U.S. Plant Pat. No. 18,469) |
|---|---|---|
| Ray floret color, upper surface: | RHS 3C | RHS 2C |
| Ray floret length: | 0.9-1.1 cm | 1.2 cm |
| Ray floret width: | 0.5-0.6 cm | 0.4 cm |
| Quantity of ray florets: | 19-21 | 13-16 |
| Quantity of discs: | 50-60 | About 80 |
| Inflorescence diameter: | 3.1-3.4 cm | 3.5-4.5 cm |
| Peduncle length: | Shorter | Longer |

Plant:

*Form, growth and habit.*—Mounded and compact, small to medium plant size, freely branching.

*Plant height.*—21.0 cm.

*Plant height (inflorescence included).*—23.0 cm.

*Plant width.*—21.0 cm.

Roots:

*Number of days to initiate and produce roots.*—20-28 days at about 22 degrees C.

*Type.*—Fine, fibrous, free branching.

*Color.*—RHS N155B.

Foliage:

*Arrangement.*—Alternate.

*Immature, leaf color, upper surface.*—Closest to RHS N138B.

*Lower surface.*—RHS 138A to RHS 138B.

*Mature, leaf color, upper surface.*—Somewhat deeper that RHS N138A.

*Lower surface.*—Closest to RHS 138A.

*Length.*—About 4-5 cm.

*Width.*—2.4-2.8 cm.

*Shape.*—Pinnate.

*Base shape.*—Attenuate.

*Apex shape.*—Broadly acute to obtuse.

*Margin.*—Pinnatisect.

*Texture, upper surface.*—Covered with very short hairs.

*Lower surface.*—Very short hair, mainly along the veins.

*Color of veins, upper surface.*—RHS 144A.

*Color of veins, lower surface.*—RHS 144B.

Stem:

*Quantity of main branches per plant.*—About 9-12.

*Color of stem.*—RHS 138C; RHS 177D basally.

*Length of stem.*—About 10-13 cm.

*Diameter.*—0.2-0.3 cm.

*Length of internodes.*—0.5-1.2 cm.

*Texture.*—Glabrous, though slightly grooved.

*Color of peduncle.*—RHS 138A to RHS 138B.

*Length of peduncle.*—About 2.5-4.0 cm.

*Peduncle diameter.*—0.15-0.2 cm.

*Texture.*—Glabrous, though slightly grooved.

Inflorescence:

*Type.*—Daisy-type inflorescences; disc and ray florets develop acropetally on a capitulum. Inflorescences held upright and outwardly on terminal peduncles.

*Quantity of inflorescences per plant.*—50-75.

*Lastingness of individual blooms on the plant.*—About 10 days.

*Fragrance.*—None.

Bud (just before opening/showing color):

*Color.*—RHS 4C.

*Length.*—0.9 cm.

*Width.*—0.6-0.8 cm.

*Shape.*—Initially round to ovate, turning cylindrical and cup-shaped with development of the rays.

Immature inflorescence:

*Diameter.*—1.8-2.5 cm.

*Color of ray florets, upper surface.*—RHS 3A to RHS 3B.

*Lower surface.*—Closest to RHS 12A.

Mature inflorescence:

*Diameter.*—3.1-3.4 cm.

*Depth.*—About 0.8 cm.

*Total diameter of 'disc'.*—1.0-1.2 cm.

*Receptacle height.*—0.6-0.8 cm.

*Receptacle diameter.*—1.1-1.3 cm.

Ray florets:

*Average quantity of florets.*—19-21 in 1-2 whorls.

*Color of florets, upper surface.*—RHS 3B to RHS 3C.

*Lower surface.*—Between RHS 4C and RHS 4D.

*Length.*—0.9-1.1 cm.

*Width.*—0.5-0.6 cm.

*Shape.*—Ligulate.

*Apex shape.*—Mucronulate to slightly praemorse.

*Margin.*—Entire.

*Texture, upper surface.*—Glabrous, smooth, slightly grooved lengthwise.

*Lower surface.*—Glabrous, smooth; with 2 protruding veins.

Disc florets:

*Average quantity of florets.*—About 50-60.

*Color of florets.*—RHS 145B with RHS 12B at the apex.

*Length.*—0.4 cm.

*Width.*—0.2 cm.

*Shape.*—Tubular, enlongated.

*Apex shape.*—Acute, 5 pointed.

Phyllaries:

*Quantity.*—About 18-25.

*Color, upper surface.*—RHS 138B with transparent margins.

*Lower surface.*—RHS 144C with transparent margins.

*Length.*—0.3-0.6 cm.

*Width.*—0.3-0.4 cm.

*Shape.*—Ovate to obovate.

*Apex shape.*—Rounded.

*Base.*—Fused.

*Margins.*—Entire.

*Texture, upper surface.*—Glabrous with papery margins.

*Lower surface.*—Glabrous with papery margins.

Reproductive organs:

Gynoecium:

*Pistil.*—1, found on both florets.

*Length.*—0.6 cm.

*Style color.*—RHS 145C.

*Style length.*—0.4 cm.

*Stigma color.*—RHS 9A.

*Stigma shape.*—Bi-furchate.

Androecium:

*Stamens.*—1, found on only disc florets.

*Color of filaments.*—RHS 2B.

*Length filaments.*—0.2 cm.

*Anther color.*—RHS 12A.

*Anther length.*—0.2 cm.

*Anther shape.*—Oval.

*Color of pollen.*—RHS 12A.

*Pollen amount.*—Moderate.

Fertility/seed set: Fertility/seed set has not been observed on this hybrid.

Disease/pest resistance: Disease/pest resistance has not been observed on this hybrid.

What is claimed is:

1. A new and distinct variety of *Argyranthemum* plant named 'Argyminyel' substantially as illustrated and described herein.

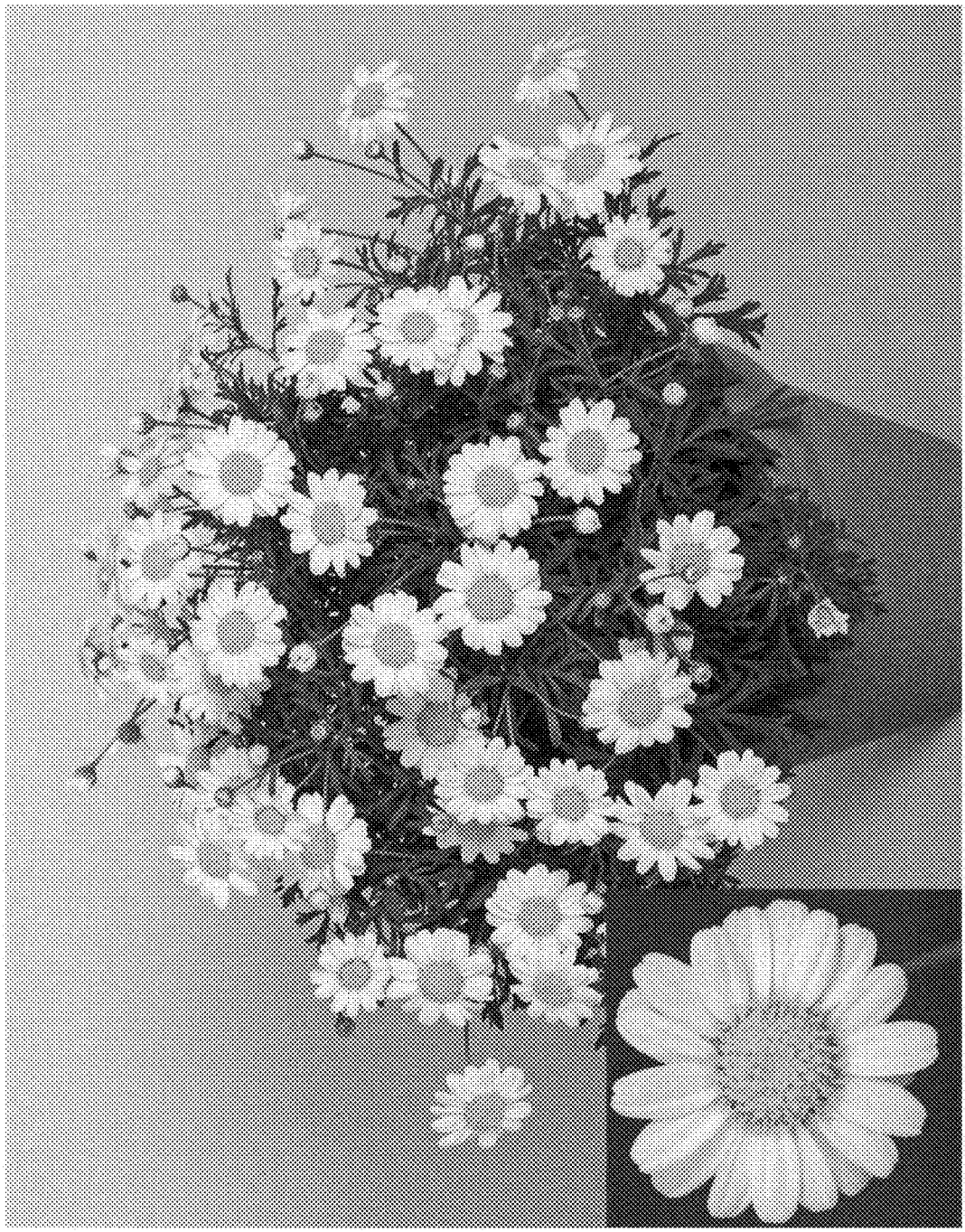

* * * * *